United States Patent [19]

Calvo

[11] 4,052,402
[45] Oct. 4, 1977

[54] PROCESS FOR SYNTHESIZING CODEINONE FROM THEBAINE

[75] Inventor: Fernando Calvo, Madrid, Spain

[73] Assignee: Fabrica de Productos Quimicos y Farmaceuticos Abello, S.A., Madrid, Spain

[21] Appl. No.: 666,663

[22] Filed: Mar. 15, 1976

[51] Int. Cl.² ............................................. C07D 489/00
[52] U.S. Cl. ................................................... 260/285
[58] Field of Search ........................................ 260/285

[56] References Cited

U.S. PATENT DOCUMENTS 3,112,323  11/1963  Krausz .................................. 260/285

Primary Examiner—Donald G. Daus
Assistant Examiner—Diana G. Rivers
Attorney, Agent, or Firm—Blanchard, Flynn, Thiel, Boutell & Tanis

[57] ABSTRACT

Codeinone is prepared by reacting thebaine with a hydrogen halide, under anhydrous conditions, in the presence of iodine as a catalyst, at a temperature of less than 10° C, hydrolyzing the reaction product and recovering codeinone.

2 Claims, No Drawings

PROCESS FOR SYNTHESIZING CODEINONE FROM THEBAINE

BACKGROUND OF THE INVENTION

1. Field of the Invention

This invention relates to a process for preparing codeinone from thebaine at a virtually quantitative yield.

2. Description of the Prior Art

The transformation of thebaine to codeinone can be carried out by a variety of different procedures.

Knorr and Horlein, Ber. 39, 1409 (1906), on the one hand, and Schopf and Hirsch, Anna. Chem. 489, 224 (1931), on the other hand, performed the hydrolysis of thebaine in an aqueous acid medium obtaining codeinone and methanol, but with very low yields.

The conversion of thebaine to codeinone via 14-bromocodeinone and neopinone was also attempted by Conroy and Krausz, J. Am. Chem. Soc., 77, 5960 (1955) and Bull, Soc. Chim. France 2148 (1960), but the number of steps required and the yield in each step make this method of little practical value.

This transformation was carried out with some success by several authors such as Gavard et al., Bull, Soc. Chim. France 1486 (1965), and has been the subject of different patents.

The yields obtained are found to be between 50% and 75%.

SUMMARY OF THE INVENTION

This invention relates to a process for transforming thebaine to codeinone by treating thebaine dissolved in an inert halogenated hydrocarbon solvent, with a hydrogen halide dissolved in an inert hydrocarbon ether solvent, particularly alkyl ethers having from one to 4 carbon atoms in the alkyl groups, under anhydrous conditions, in the presence of a catalyst, preferably iodine, and the subsequent hydrolysis of the halogenated compound thus formed in an aqueous alkaline medium at working temperatures lower than 10° C. The hydrogen halide is preferably hydrogen bromide or hydrogen chloride, and hydrogen bromide is especially preferred.

Yields of higher than 95% are obtained by the process of the invention.

In order to illustrate a preferred mode of performing this invention, there is set forth the following non-limiting example.

EXAMPLE:

To a 3-liter flask equipped with an agitator, a thermometer and a gas outlet tube containing calcium chloride, which flask contains a solution of 150 g of anhydrous hydrogen bromide dissolved in 550 ml of n-dibutyl ether and is externally cooled at −15° C, there is added a solution of 2 g of iodine dissolved in 100 ml of anhydrous methylene chloride, and the temperature is then reduced to −20° C.

When this temperature is reached, a solution of 100 g of thebaine (purity : 92.5%) dissolved in 1,000 ml anhydrous methylene chloride previously cooled at −15° C is rapidly added with vigorous agitation to the former solution.

As a consequence of this addition, the temperature rises to +10° C. It is reduced to 0° C in a short time by external cooling and this temperature is maintained for 7 minutes.

At the end of this period the content of the flask is poured with vigorous agitation into a 5-liter flask containing a suspension of 180 g sodium bicarbonate in 1,000 g of water and 450 g of ice.

The agitation is maintained for one hour. the hydrolysis reaction product separates into two layers. The aqueous layer is adjusted to pH 8 with dilute soda and is extracted three times, each time with 200 ml methylene chloride. The combined extracts are added to the organic layer, and the organic mixture is washed with water and dried with anhydrous sodium sulfate.

From the resulting solution, the methylene chloride solvent is evaporated under vacuum until its volume is reduced to 1/100 of the original volume.

The codeinone which precipitates during concentration of the organic solution, which exhibits a clear pink color, is then filtered and washed with diethyl ether.

There is obtained 96 g codeinone of m.p. 165°-7° C and with a purity of 90.36%. The yield was 98%.

The embodiments of the invention in which an excluse property or privilege is claimed are defined as follows:

1. A process for preparing codeinone, which comprises the steps of: reacting thebaine dissolved in an inert halogenated hydrocarbon solvent, with hydrogen chloride or hydrogen bromide dissolved in an inert alkyl ($C_1$ to $C_4$) ether solvent, in the presence of iodine as a catalyst, under anhydrous conditions, to form a halogenated reaction product, then hydrolyzing the halogenated reaction product with an aqueous solution of sodium bicarbonate to transform the halogenated reaction product to codeinone, the reacting and hydrolyzing steps being carried out at temperatures below about 10° C, and recovering codeinone from the product of the hydrolysis step.

2. A process as claimed in claim 1 in which said inert halogenated hydrocarbon solvent is methylene chloride, said hydrogen halide is hydrogen bromide, said inert hydrocarbon ether solvent is di(n-butyl)ether, the product of the hydrolysis step is separated into an aqueous layer and an organic layer containing codeinone dissolved in methylene chloride and codeinone is recovered from the organic layer by evaporating methylene chloride.

* * * * *